United States Patent [19]

Scharnberg

[11] Patent Number: 5,123,423

[45] Date of Patent: * Jun. 23, 1992

[54] DEFIBRILLATOR PAD ASSEMBLY AND METHOD FOR USING SAME

[75] Inventor: Lorne C. Scharnberg, West Des Moines, Iowa

[73] Assignee: KAS Products, Inc., Des Moines, Iowa

[ * ] Notice: The portion of the term of this patent subsequent to Mar. 12, 2008 has been disclaimed.

[21] Appl. No.: 663,557

[22] Filed: Mar. 4, 1991

Related U.S. Application Data

[63] Continuation-in-part of Ser. No. 456,497, Dec. 26, 1989, Pat. No. 4,998,536.

[51] Int. Cl.⁵ .............................................. A61N 1/04
[52] U.S. Cl. ................................... 128/798; 128/800; 128/802
[58] Field of Search ............... 128/798, 800, 802, 803; 606/32

[56] References Cited

U.S. PATENT DOCUMENTS

| | | | |
|---|---|---|---|
| 4,239,046 | 12/1980 | Ong | 128/798 X |
| 4,267,840 | 5/1981 | Lazar et al. | 606/32 |
| 4,779,630 | 10/1988 | Scharnberg et al. | 128/798 X |
| 4,867,166 | 9/1989 | Axelgaard et al. | 128/798 X |
| 4,998,536 | 3/1991 | Scharnberg | 128/800 |

FOREIGN PATENT DOCUMENTS

| | | | |
|---|---|---|---|
| 1115351 | 12/1981 | Canada | 128/798 |
| 2814061 | 10/1978 | Fed. Rep. of Germany | 606/32 |

*Primary Examiner*—Lee S. Cohen
*Attorney, Agent, or Firm*—Zarley, McKee, Thomte, Voorhees & Sease

[57] ABSTRACT

The defibrillator pad of the present invention comprises a lower layer of electrically conductive tacky polymer and an upper layer of filamentous carbon fabric containing carbon fibers coated with an electrically conductive polymer. The pad is placed on the patient's chest with the polymer layer facing downwardly in contact with the patient's chest and with the carbon layer facing upwardly for engagement with the electrodes of the defibrillator paddles.

12 Claims, 1 Drawing Sheet

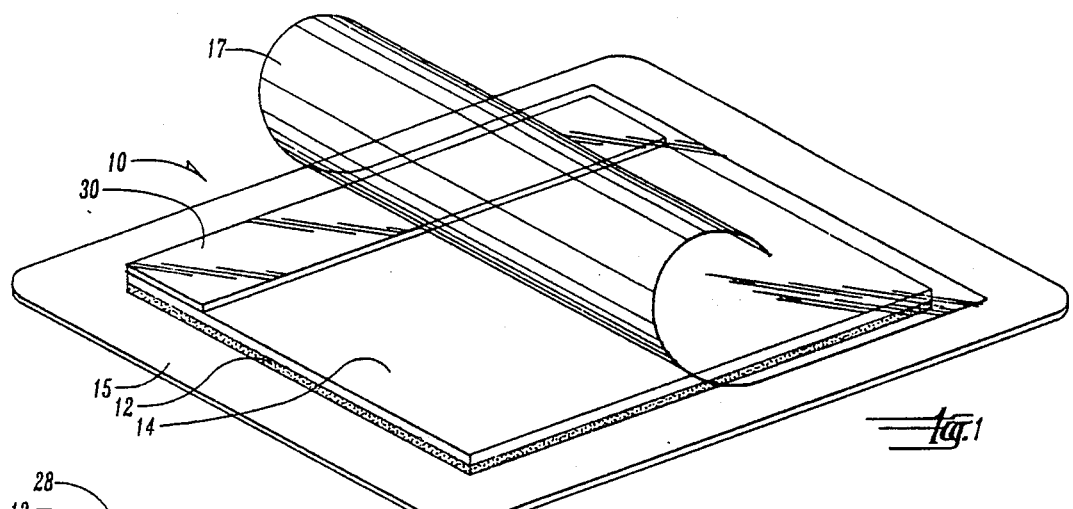
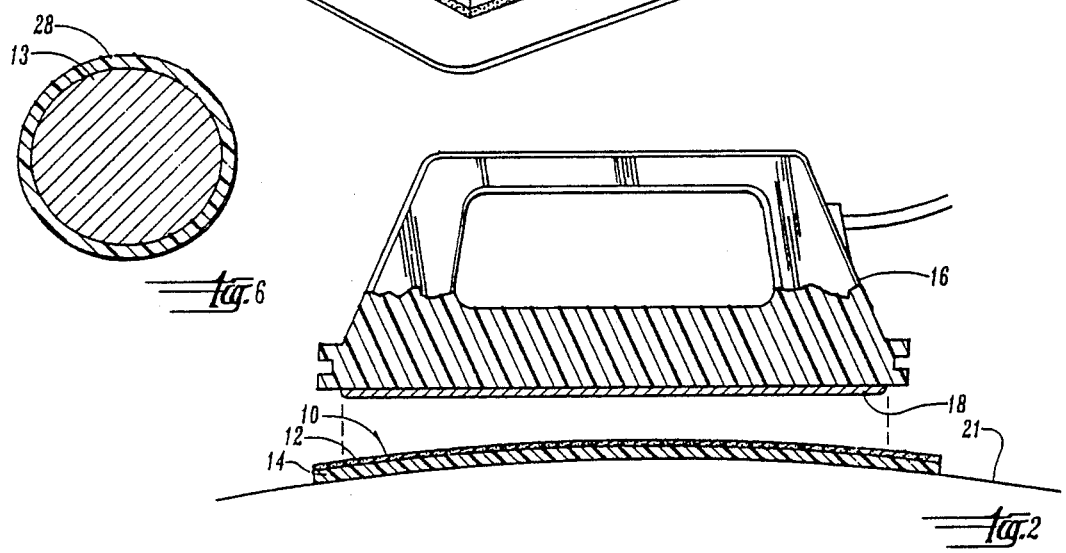
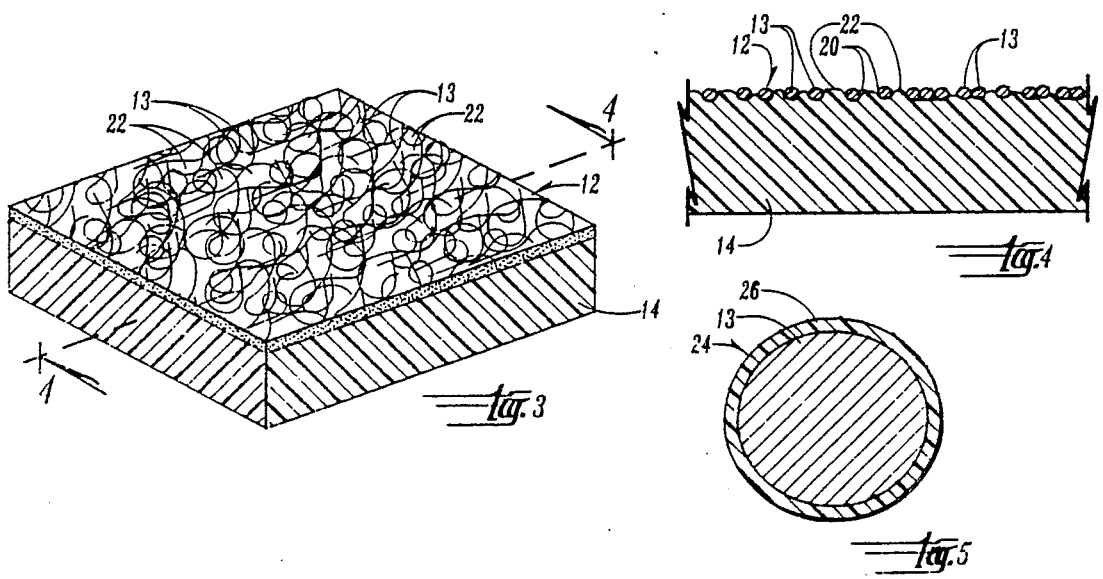

DEFIBRILLATOR PAD ASSEMBLY AND METHOD FOR USING SAME

BACKGROUND OF THE INVENTION

This is a continuation-in-part of copending application Ser. No. 456,497, filed Dec. 26, 1989, now U.S. Pat. No. 4,998,536.

This invention relates to a defibrillator pad assembly and a method for using same.

Defibrillation is a process used for patients encountering fibrillation of the heart. The defibrillation process involves placing two electrode paddles on the patient's chest and applying a high density, electrical current to the patient so as to stimulate the heart and correct the fibrillation of the heart.

Dry skin on a patient causes the interface between the metal defibrillator paddles and the skin to have a high impedance. This can cause severe skin burns and may cause a significant reduction in the current delivered to the heart so as to prevent successful defibrillation.

Present methods for applying the defibrillator paddles to the skin involve the use of electrically conductive gels which are applied to the patient's skin and which are also applied to the defibrillator paddles. Often the gel is incompletely applied leaving bare spots between the paddle and the patient's. These bare spots may result in burning of the patient's skin during discharge. Also, it is necessary for the user of the paddles to continue to apply pressure between the paddle and the patient's skin in order to insure a positive electrical contact therebetween.

Another disadvantage of presently used gels is that they are messy. Also, the gel often gets on the user's hands and arms, making it difficult for the user to perform other functions such as cardiopulmonary resuscitation.

Another presently used method for defibrillating involves the use of moisturized polymer pads which are enclosed within an airtight envelope. The pads are removed from the envelope and placed on the patient's chest immediately prior to use. Then the defibrillator paddles are placed over the pads in preparation for their use. The disadvantage of these moisturized pads is that they tend to harden and become brittle after prolonged exposure to the atmosphere. Furthermore, they do not provide a strong adhesive bond between the pad and the patient's chest, and therefore, they sometimes slip or move after use.

Another method for defibrillating involves the use of a pad such as disclosed in U.S. Pat. No. 4,779,630. The method disclosed in this patent shows a polymer pad which is tacky and adhesive in its characteristics. It is also a good electrical conductor. The polymer pad is placed over the electrode on the defibrillator paddle. Then the paddle with the polymer pad thereon is placed over the patient's chest. The tackiness of the polymer pad causes the defibrillator paddle to adhere to the pad and also causes the polymer pad to adhere to the patient's chest, thereby providing a good electrical contact between the paddle and the chest.

Therefore, a primary object of the present invention is the provision of an improved defibrillator pad assembly and method for using same.

A further object of the present invention is the provision of a defibrillator pad assembly which utilizes conductive pads having a tacky undersurface, but having an upper surface which is substantially less tacky so that the defibrillator paddles can be easily removed from the pad.

A further object of the present invention is the provision of an improved defibrillator pad assembly which utilizes pads which can be quickly adhered to the patient's chest and left there for a period of time during transporting of the patient.

A further object of the present invention is the provision of an improved defibrillator pad having an adhesive electrically conductive polymer on its lower surface and having a layer of filamentous carbon fabric on its upper surface.

A further object of the present invention is the provision of an improved defibrillator pad assembly and method for using same which is economical, efficient in operation, and inexpensive.

SUMMARY OF THE INVENTION

The present invention utilizes a laminated pad comprising a conductive polymer layer and a conductive filamentous carbon layer. The polymer layer is on the bottom of the pad, and is preferably a conductive polymer which can be purchased from Promeon Division of Medtronic, Inc., 6951 Central Avenue, N.E., Minneapolis, Minn. 55440, under the product designation RG 63 A, RG 36 B, or RG 36 T, the latter being the preferred polymer. The conductive polymer includes thin fibers of polyethylene scrim which run through the polymer and which give the polymer sheets strength. The scrim may also be made of other materials such as carbon, nickel, coated-carbon, or other materials.

The conductive pad is shaped to fit the metal electrodes of the paddle, or it can be slightly larger than the electrodes of the paddles. The conductive pad has a strong tacky characteristic which causes it to adhere to the patient's skin, but the filamentous carbon upper layer is less tacky, thereby permitting the defibrillator paddles to be placed on the defibrillator pad and removed from the defibrillator pad a plurality of times.

The filamentous carbon layer is preferably a nonwoven fabric comprising 100 percent carbon fibers, and having a density of approximately 0.35 ounces per square yard to 0.5 ounces per square yard. The filamentous fiber fabric provides good electrical conductivity, and it also permits small protrusions of the polymer there below to protrude upwardly through voids which are in the filamentous carbon fabric. This provides a mild tackiness to the upper surface, so as to minimize the tendancy of the defibrillator paddle to slip.

If the filamentous carbon layer is uncoated, there is a possibility that minor sparking may occur between the various carbon fibers during defibrillation. While this minor sparking does not affect the defibrillation process, it is a concern to physicians and paramedics because the sparking could create safety hazards in an environment where oxygen or other volatile materials might be used. In order to minimize the risk of sparking, the filamentous carbon mesh is soaked in a liquid solution of conductive polymer so as to thoroughly wet the filamentous carbon fiber. The fiber is then removed from the solution and permitted to dry. After drying, the various fibers within the filamentous carbon fiber fabric are coated with the conductive polymer. It has been found that treating the filamentous carbon fiber fabric in this manner reduces and in nearly all cases eliminates the sparking between the carbon fibers during defibrillation.

Any conductive polymer will work in the above method so long as it does not react to the carbon during the soaking operation. The preferred conductive polymer is a custom made product purchased from Promeon division of Medtronic, Inc., 6951 Central Avenue, N.E., Minneapolis, Minn. 55440, under the trade designation "5% Poly NaAMPS". This product is diluted with water in a ratio of nine parts water to one part polymer by volume. It is then put into a container to which the carbon fibers are added and soaked. After the soaking of the fibers, the fibers are rolled out on a table and allowed to dry.

A modified form of the invention utilizes an upper layer of nickel-coated filamentous fibers. The nickel coating of the carbon fibers slightly enhances the electrical conductivity of the fabric.

Normally the defibrillator pad of the present invention is stored between a bottom release liner and a top release liner to maintain the adhesiveness of the pad and to prevent dirt or other materials from adhering to the pad. The release liners are each treated with a silicone film which permits them to be separated easily from the tacky polymer of the defibrillator pad. When it is desired to use the pad, the top release liners are removed from the pad, and the pad itself is removed from the bottom release liner. The pad is then placed on the patient's chest with the polymer facing down so as to cause the pad to adhere to the patient's chest. Tackiness of the polymer will cause the pad to remain on the patient's chest without further aid from the operator. The operator then takes the defibrillator paddle and places the electrode of the paddle downwardly on the upwardly presented carbon surface of the defibrillator pad. Electrical continuity is provided between the defibrillator electrode and the patient's chest by virtue of the laminated structure of the upper layer of carbon fabric and the lower layer of polymer which comprise the defibrillator pad.

After the defibrillator paddle has been used to provide an electrical shock to the patient, the paddle can be removed easily due to the minimal tackiness which is presented on the upper surface of the laminated pad. A certain minimal amount of tackiness is, however, provided due to the fact that there are certain voids in the carbon fabric which permit the polymer to exude upwardly and be partially exposed through the filamentous carbon. This minimal tackiness prevents the paddles from sliding laterally during their operation, but the tackiness is slight enough to permit easy removal of the paddles after the paddles have been used.

The defibrillator pads can be left on the patient's skin during transporting to the hospital so that they will be in place in the event a second defibrillation operation is required.

BRIEF DESCRIPTION OF THE DRAWINGS

FIG. 1 is a perspective view of the defibrillator pad of the present invention.

FIG. 2 is a partial sectional view showing the defibrillator pad on a patient's chest with a defibrillator paddle positioned upwardly above the patient.

FIG. 3 is an enlarged partial perspective view showing the voids in the upper filamentous carbon layer of fabric.

FIG. 4 is a sectional view taken along line 4—4 of FIG. 3.

FIG. 5 is a sectional view showing a modified form of carbon fiber utilizing a nickel coating on the outer surface thereof.

FIG. 6 is a sectional view of a carbon fiber which has been coated with a conductive polymer.

DESCRIPTION OF THE PREFERRED EMBODIMENT

Referring to the drawings, the numeral 10 generally designates the defibrillator pad of the present invention. Pad 10 comprises an upper carbon fabric layer 12 and a lower polymer layer 14. Pad 10 is shown packaged between a bottom release liner 15 and a transparent top release liner 17. Release liners 15, 17 are treated with a silicone film so that they can be easily removed from pad 10.

The lower polymer layer 14 is a conductive polymer purchased from Promeon Division of Medtronic, Inc., 8299 Central Avenue, N.E., Minneapolis, Minn. 55432, under the product designation RG 63 A, or RG 63 B. The conductive polymer includes thin fibers of polyethylene scrim which run through the polymer and which give the polymer sheet strength. The scrim may also be made of other materials such as carbon, nickel-coated carbon, or other materials.

The upper carbon layer is comprised of a fabric made from a plurality of individual carbon fibers 13. The fibers 13 are preferably not woven, but are matted together in an irregular configuration. Preferably the fabric is very thin, having a density of 0.35 ounces to 0.5 ounces per square yard. Due to the thinness of the carbon layer 12, the polymer of the lower polymer layer 14 exudes upwardly through small openings or voids 20 so as to create a plurality of protrusions 22 of polymer which are exposed upwardly through the fabric. The existence of the carbon fabric over the top of the polymer inhibits the tacky characteristics of the polymer on its upper surface so that it will not stick or adhere strongly to another object. However, the fact that some protrusions 22 of the polymer protrude through the carbon fabric gives the carbon fabric a slightly tacky or nonslip surface.

If the filamentous carbon layer is uncoated, there is a possibility that minor sparking may occur between the various carbon fibers during defibrillation. While this minor sparking does not affect the defibrillation process, it is a concern to physicians and paramedics because the sparking could create safety hazards in an environment where oxygen or other volatile materials might be used. In order to minimize the risk of sparking, the filamentous carbon mesh is soaked in a liquid solution of conductive polymer so as to thoroughly wet the filamentous carbon fiber. The fiber is then removed from the solution and permitted to dry. After drying, the various fibers within the filamentous carbon fiber fabric are coated with the conductive polymer. It has been found that treating the filamentous carbon fiber fabric in this manner reduces and in nearly all cases eliminates the sparking between the carbon fibers during defibrillation.

Any conductive polymer will work in the above method so long as it does not react to the carbon during the soaking operation. The preferred conductive polymer is a custom made product purchased from Promeon division of Medtronic, Inc., 6951 Central Avenue, N.E., Minneapolis, Minn. 55440, under the trade designation "5% Poly NaAMPS". This product is diluted with water in a ratio of nine parts water to one part polymer by volume. It is then put into a container to which the carbon fibers are added and soaked. After the soaking of the fibers, the fibers are rolled out on a table and allowed to dry. Referring to FIG. 6, a typical carbon fiber 13 is shown having the conductive polymer 28 coated thereon.

FIG. 2 illustrates the manner in which the device is used. When it is desired to defibrillate a patient, the transparent layer 17 is peeled back and removed as shown in FIG. 1. Then the pad 10 is peeled off of the backing layer 15, and is placed on the exposed skin surface 21 of a patient's chest as shown in FIG. 2. A thin strip 30 of non-tacky material is superimposed over the polymer layer 14 along one edge thereof so as to permit the operator to grasp pad 10 without encountering the tackiness of polymer layer 14. The polymer layer is placed downwardly in contact with the skin surface 21 of the patient's chest, and its tackiness causes it to adhere to the skin surface tightly so as to provide a positive electrical connection therewith.

Then a defibrillator paddle 16 having an electrode surface 18 is placed on top of the carbon layer 12 as shown in FIG. 2. Placing the electrode 18 in electrical contact with the carbon layer 12 provides electric continuity through the carbon layer 12 and the polymer layer 14 to the patient's chest. While the electrode 18 does not stick strongly to the pad, the fact that small mounds or protrusions 22 of the polymer exude through the voids 20 in the carbon layer provides a substantially nonslip surface for the electrode 18.

The electrode is then used to defibrillate the patient, and then it can be removed from the patient after the defibrillation is complete. The pads 10 stay in place on the patient, and can be kept in place until the danger of further fibrillation has passed. If defibrillation is needed a second time, all that is necessary is to replace the paddles on the carbon layers 12 and repeat the defibrillation process.

The present invention provides the important features of repeatability and dependability. The defibrillation process can be repeated numerous times with equally good results due to the good electrical contact which is obtained through the carbon layer 12 and the polymer 14. Furthermore, the device is dependable in that because of good electrical contact being made the defibrillation process occurs without burning or damaging the patient.

Referring to FIG. 5, modified form 24 of the carbon filaments is shown, wherein each carbon filament 13 includes a nickel coating 26 on the outer surface thereof. The nickel coating enhances the electrical conductivity of the pad. While 100 percent carbon fabric will work satisfactorily, the nickel coating improves the conductivity by approximately two to five percent.

If nickel coating is used for the fibers, it is possible to use a material other than carbon for the fibers themselves since the nickel will provide the electrical conductivity necessary to provide a repeatable and dependable defibrillation. Thus, it can be seen the device accomplishes at least all of its stated objectives.

I claim:

1. A method for preparing a patient's chest having an exposed skin surface for accepting a defibrillator paddle, said method comprising:

taking a laminated defibrillator pad having a bottom layer of electrically conductive polymer which is tacky so as to adhere to most surfaces it contacts, said pad having an upper layer comprising fabric material formed from filamentous carbon fibers which are coated with a film of electrically conductive polymer, said upper layer being adhered to and in electrical contact with said bottom layer;

placing said pad on said patient's chest with said bottom layer in contact with said exposed skin surface of said patient's chest whereby said tackiness of said bottom layer will cause said pad to be detachably adhered to and in electrical contact with said exposed skin surface of said patient's chest; and placing said defibrillator paddle in facing engagement with and in electrical contact with said upper layer of said pad whereby said pad will provide electrical continuity from said defibrillator paddle to said exposed skin surface of said patient.

2. A method according to claim 1 and further comprising removing said defibrillator paddle from electrical contact with said upper layer of said pad, said upper layer at least partially shielding said defibrillator paddle from said tackiness of said bottom layer whereby said pad will remain adhered to said exposed skin surface after removal of said defibrillator paddle from said upper surface.

3. A method according to claim 2 and further comprising using pure carbon for said filamentous carbon fibers of said upper layer.

4. A method according to claim 2 and further comprising using nickel plated carbon for said filamentous carbon fibers of said upper layer.

5. A defibrillator pad for use between an exposed skin surface of a patient's chest and a planar electrode surface of a defibrillator paddle, said defibrillator pad comprising:

a laminated defibrillator pad having a bottom layer and an upper layer;

said bottom layer being comprised of an electrically conductive polymer which is tacky so as to adhere to most surfaces it contacts;

said upper layer comprising fabric material formed from filamentous carbon fibers, said fabric material having a plurality of openings therein;

said bottom layer having a flat downwardly presented surface for engaging and adhering to said patient's chest with a first predetermined force, and having an upwardly presented upper surface in contact with said upper layer;

said conductive polymer of said upper surface of said bottom layer exuding through said openings of said upper layer so as to form a plurality of polymer protrusions which are exposed upwardly through said openings of said upper layer;

said polymer protrusions and said fabric of said upper layer combining to form an upwardly presented planar electrode engaging surface capable of engaging and covering said electrode surface of said defibrillator paddle and capable of adhering to said electrode surface with a force less than said first predetermined force at which said downwardly presented surface of said defibrillator pad will adhere to said exposed skin surface of said patient's chest.

6. A defibrillator pad according to claim 5 wherein said upper layer comprises 100 percent carbon.

7. A defibrillator pad according to claim 5 wherein said upper layer comprises nickel-plated carbon.

8. A defibrillator pad according to claim 5 wherein said fabric material comprises carbon fibers having a density of from 0.35 ounces per square yard to 0.5 ounces per square yard.

9. A defibrillator pad according to claim 5 wherein said filamentous carbon fibers of said upper layer are coated with a film of electrically conductive polymer.

10. A defibrillator pad according to claim 5 wherein said fabric material of said upper layer comprises a plurality of said filamentous carbon fibers matted together in an irregular configuration.

11. A defibrillator pad according to claim 5 wherein said fabric material has a density of from 0.35 ounces to 0.5 ounces per yard.

12. A combination adapted to be applied to an exposed skin surface of a patient's chest comprising:

a laminated defibrillator pad having a bottom layer of electrically conductive polymer which is tacky so as to adhere to most surfaces it contacts, said pad having an upper layer comprising fabric material formed from filamentous carbon fibers which are coated with a film of electrically conductive polymer;

said bottom layer being adapted to be in contact with said exposed skin surface of said patient's chest whereby said tackiness of said bottom layer causes said bottom layer to be detachably adhered to and in electrical contact with said exposed skin surface;

said upper layer having openings therein;

said bottom layer exuding upwardly through said openings so as to create a plurality of protrusions which are exposed upwardly through said openings of said upper layer;

a defibrillator paddle having an electrode surface in facing engagement with and in electrical contact with said upper layer of said pad and said protrusions of said bottom layer which are exposed upwardly through said openings of said upper layer;

said upper layer at least partially shielding said defibrillator electrode surface from said tackiness of said bottom layer whereby said electrode surface adheres to said defibrillator pad with an adhering force which is less than the adhering force between said bottom layer and said exposed surface of said patient's skin.

* * * * *